(12) United States Patent
Ino et al.

(10) Patent No.: US 8,500,755 B2
(45) Date of Patent: Aug. 6, 2013

(54) APPARATUS AND METHOD FOR DELIVERING FASTENERS DURING VALVE REPLACEMENT

(75) Inventors: Takashi Harry Ino, San Jose, CA (US);
Michael J. Drews, Palo Alto, CA (US);
Donnell W. Gurskis, Belmont, CA (US)

(73) Assignee: Medtronic, Inc., Minneapolis, MN (US)

( * ) Notice: Subject to any disclaimer, the term of this patent is extended or adjusted under 35 U.S.C. 154(b) by 1275 days.

(21) Appl. No.: 12/022,898

(22) Filed: Jan. 30, 2008

(65) Prior Publication Data
US 2008/0119875 A1     May 22, 2008

Related U.S. Application Data

(63) Continuation of application No. 11/004,445, filed on Dec. 3, 2004, now abandoned.

(51) Int. Cl.
*A61B 17/10*        (2006.01)
(52) U.S. Cl.
USPC ........................................................... 606/143
(58) Field of Classification Search
USPC . 606/141–143, 213, 219, 75, 221; 227/175.1, 227/19; 411/439–499; 29/611.2, 24
See application file for complete search history.

(56) References Cited

U.S. PATENT DOCUMENTS

| | | | | |
|---|---|---|---|---|
| 5,725,554 A | * | 3/1998 | Simon et al. | 606/219 |
| 2005/0192628 A1 | * | 9/2005 | Viola | 606/219 |
| 2005/0274768 A1 | * | 12/2005 | Cummins et al. | 227/175.1 |

* cited by examiner

*Primary Examiner* — Ryan Severson
*Assistant Examiner* — Tin Nguyen

(57) ABSTRACT

A fastener delivery tool includes a loading chamber for receiving a fastener having a pair of tines overlapping one another to define a loop in a parent or relaxed state. A retaining member retains the fastener in the loading chamber. The fastener delivery tool also includes a tongue, pusher member, and an ejection track communicating with the loading chamber. An actuator causes the tongue to move to engage the tines of the fastener to transform the fastener from the relaxed state to a constrained state defining a U-shape. The actuator also causes the pusher member to release the retaining member and advance the fastener down the ejection track in the constrained state. The tool also includes a trigger for ejecting the fastener completely from the ejection track. The fastener may be used to secure a prosthetic heart valve or components thereof into surrounding tissue, e.g., within a tissue annulus.

18 Claims, 17 Drawing Sheets

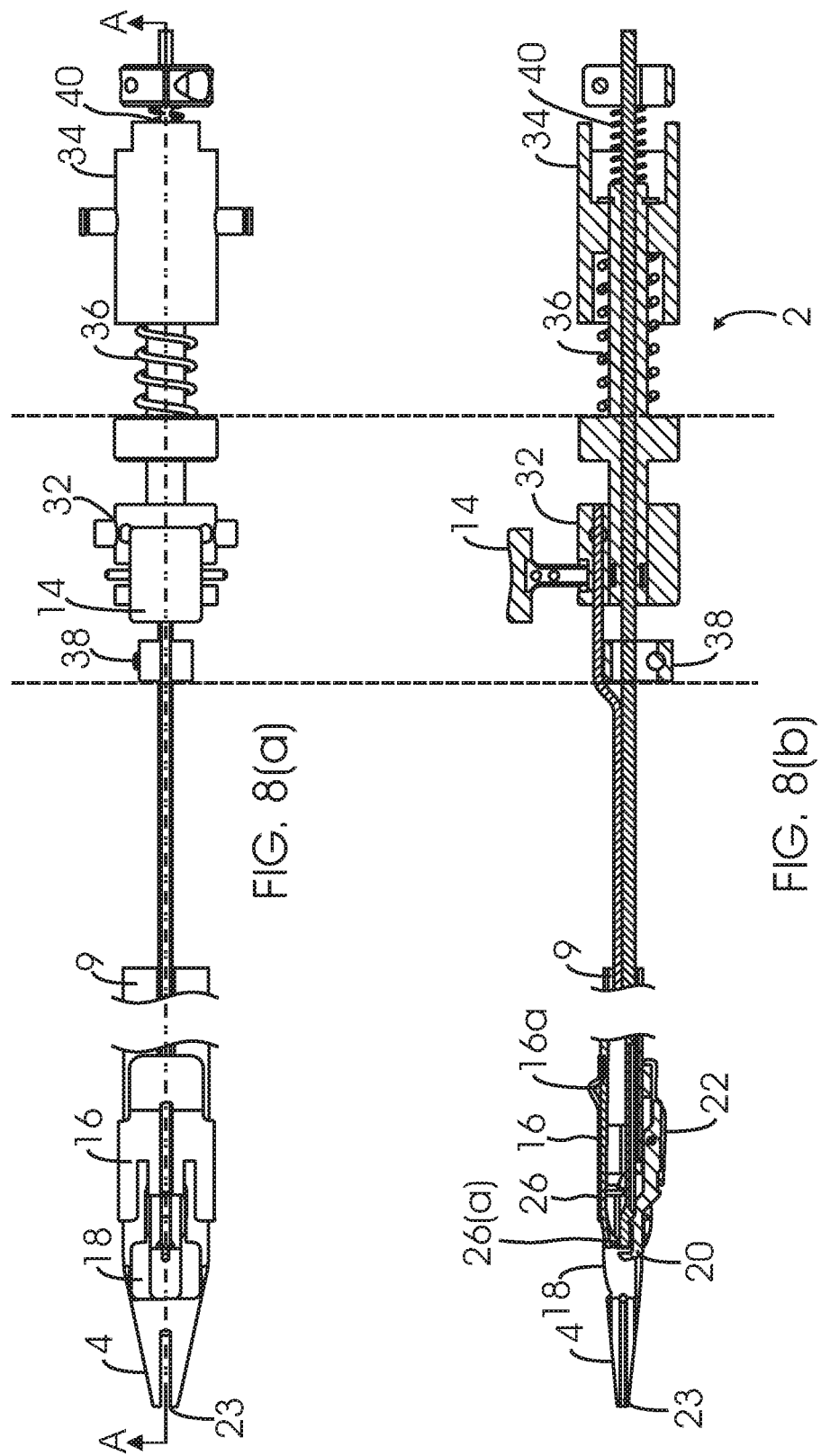

FIG. 9(b) Section B-B

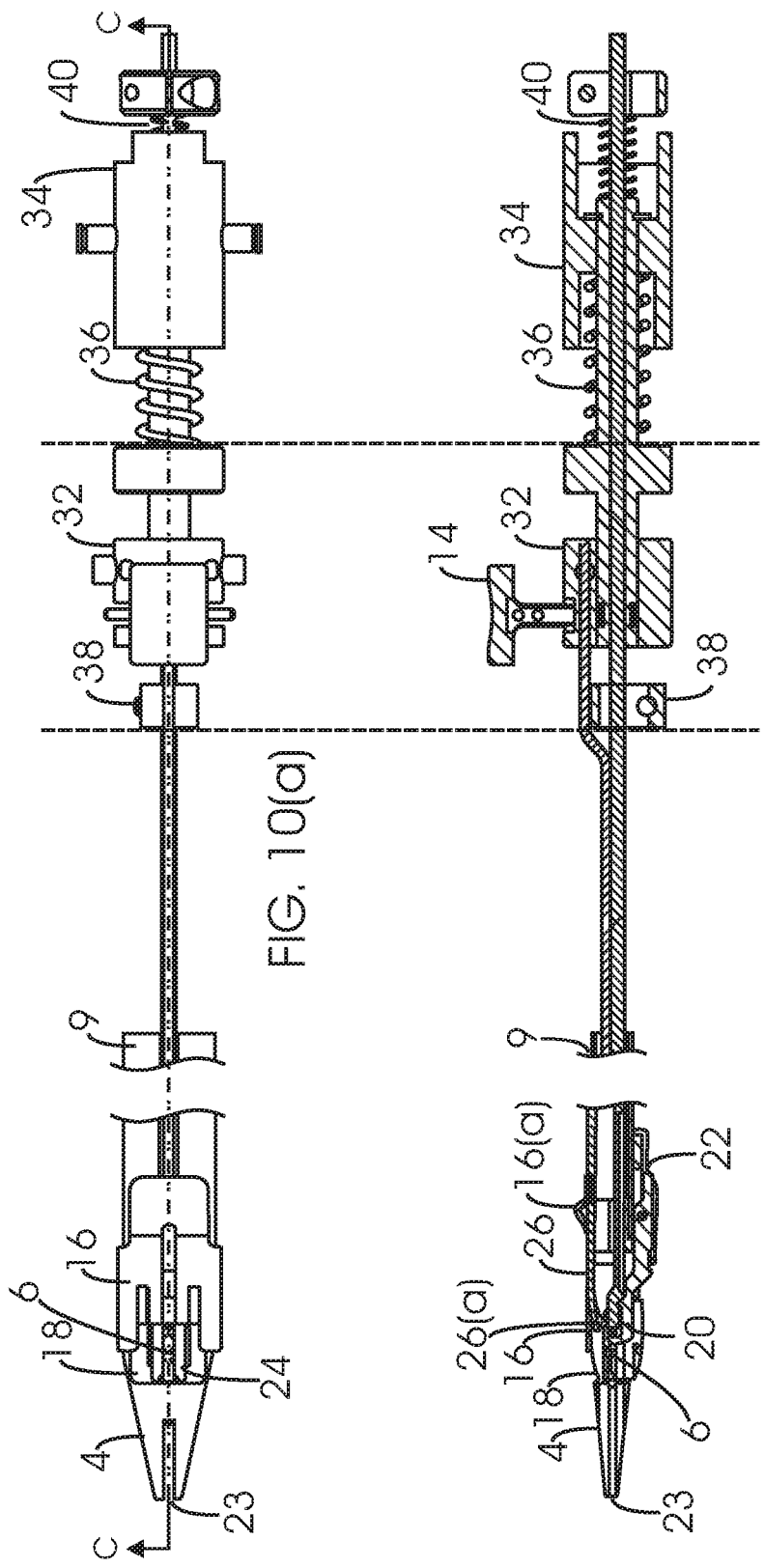

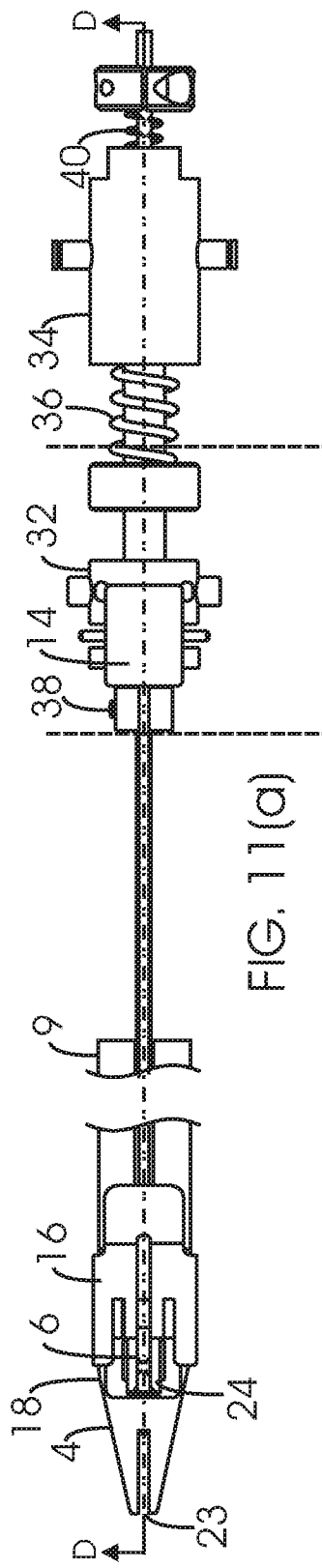
FIG. 11(a)
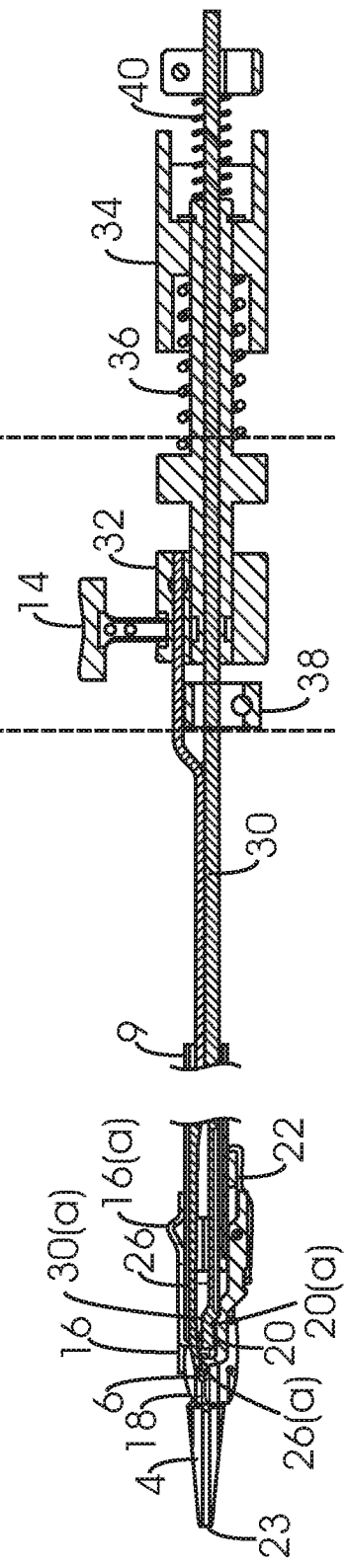
FIG. 11(b) Section D-D

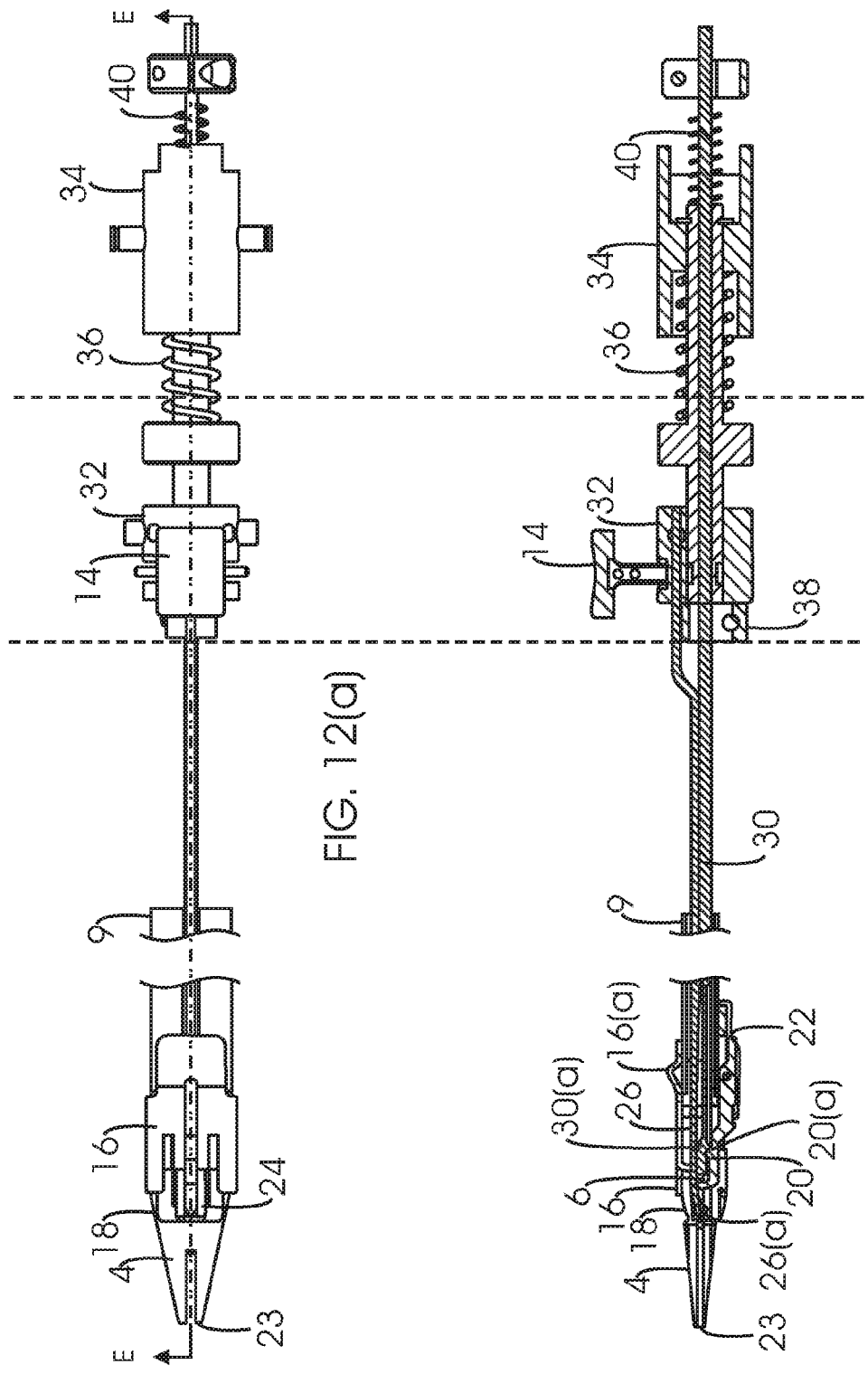

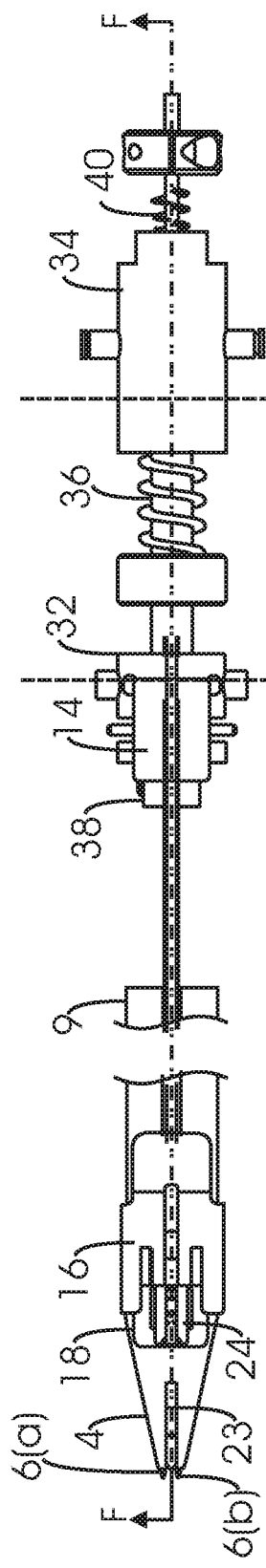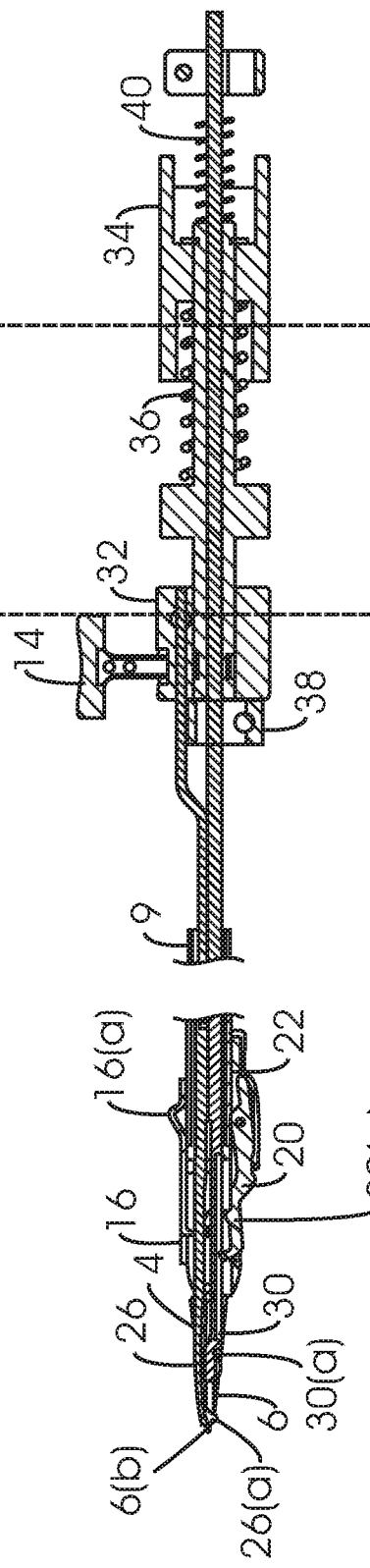
FIG. 13(a)
FIG. 13(b) Section F-F

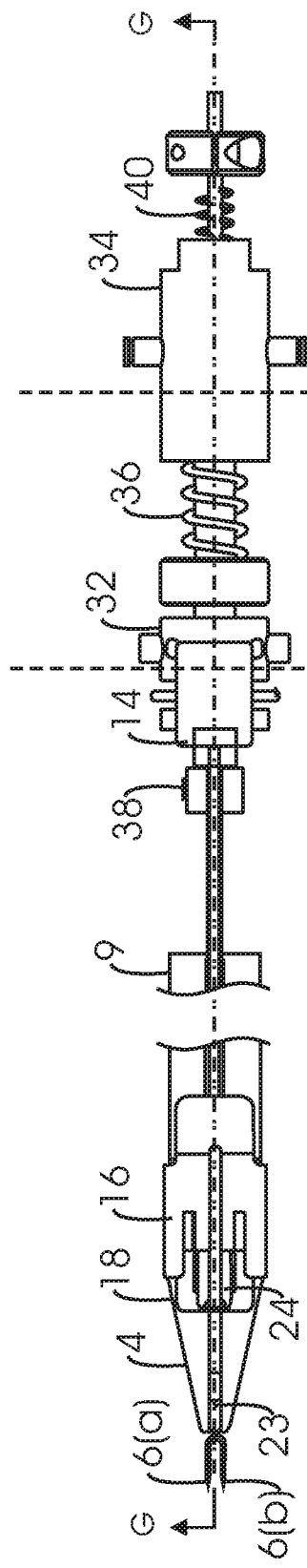
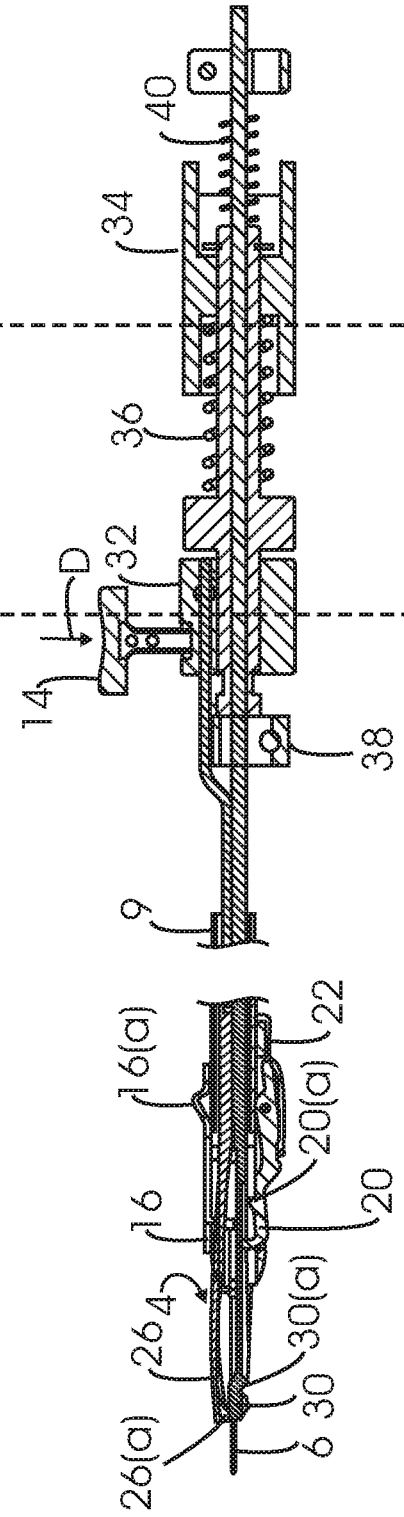
FIG. 14(a)
FIG. 14(b) Section G-G

APPARATUS AND METHOD FOR DELIVERING FASTENERS DURING VALVE REPLACEMENT

This application is a continuation of co-pending application Ser. No. 11/004,445, filed Dec. 3, 2004.

FIELD OF THE INVENTION

The invention relates generally to apparatus and methods for fastening devices to tissue or other devices, and, more particularly, to apparatus and methods for delivering fasteners during heart valve replacement, placement of other prostheses, or repair of body organs in general and vascular surgery, such as wound closure, anastomosis, hernia repair, and grafting procedures for aneurysm repair.

BACKGROUND

Prosthetic heart valves have been used to replace defective human valves in patients. A prosthetic valve generally includes a sewing ring or suture cuff that may be attached to and/or extend around a valve member. The sewing ring may be made from a biocompatible fabric and/or other material through which a needle and suture may pass. The sewing ring may be part of a single piece prosthetic valve, or may be part of a multiple piece prosthetic valve assembly.

In a typical aortic valve replacement procedure, the aorta may be incised and the defective valve leaflets removed, leaving a desired placement site that may include a fibrous tissue layer or tissue annulus. Needles carrying sutures may be directed through the fibrous tissue or desired placement site within the tissue annulus to form an array of sutures. Free ends of the sutures may be extended out of the thoracic cavity and laid, spaced apart, on the patient's body.

The needles and sutures may then be threaded individually through a sewing ring, typically delivering between ten and twenty (12-20) sutures through the sewing ring. Once the sutures have been directed through the sewing ring, the sutures may be pulled up taught and the sewing ring may be slid over the sutures or "parachuted" down into place adjacent the placement site tissue. The sewing ring may then be secured in place by knot tying knots in the sutures. This procedure is time consuming as doctors often use three to ten knots per suture.

If the sewing ring is separate from a valve member of a multiple component prosthesis, the valve member may be introduced into the placement site, and secured to the sewing ring. The sutures may be tied, not only to secure the sewing ring to the biological mass and, but to secure the valve member to the sewing ring (and consequently, to the tissue annulus).

During heart valve replacement procedures, the patient may be on cardiopulmonary bypass (CPB), which may reduce the patient's oxygen level and/or create non-physiological blood flow dynamics. The longer a patient is on CPB, the greater the risk for long-term or even permanent health damage. Existing suturing techniques extend the duration of CPB and, consequently, increase the health risks due to the patient. Furthermore, the fixturing force created by suturing varies significantly from suture to suture, even for the same medical professional.

Sewing rings can also be tedious and time consuming to secure to a valve orifice. To assemble multiple component heart valves, for example, one component has to be sewn into another in vivo, resulting in a complex and time consuming process. The complexity of the procedure also provides a greater opportunity for mistakes and requires a patient to be on cardiopulmonary bypass for a lengthy period.

SUMMARY OF THE INVENTION

The invention is directed to apparatus and methods for fastening devices to tissue or other devices, and, more particularly, to apparatus and methods for delivering fasteners during heart valve replacement. The invention may be deployed to secure a prosthesis to surrounding tissue, or to secure one prosthesis to another, or a portion of a prosthesis to a coordinating prosthesis.

In accordance with one embodiment, a fastener delivery tool is provided that includes a loading chamber for receiving a fastener having a plurality of tines in a relaxed state. The tool also includes a releasable retaining member for limiting movement of the fastener within the loading chamber. An ejection track is coupled to the loading chamber. A handle is provided that includes a lever, and a tongue and pusher member coupled to the lever. Movement of the lever advances the tongue to engage the tines so as to transform the fastener from the relaxed state to a constrained state. Movement of the lever also advances the fastener from the loading chamber down the ejection track. A trigger is depressed to eject the fastener from the tool.

In another embodiment, a method for delivering a fastener is provided that includes providing a fastener delivery tool having a fastener therein, the fastener including a pair of tines in a relaxed state. The fastener is secured in the fastener delivery tool using a releasable retaining member. A tongue is advanced in the fastener delivery tool so as to transform the fastener from a relaxed state to a constrained state while the fastener is secured with the releasable retaining member. The retaining member is released and the fastener is advanced in the constrained state distally within the fastener delivery tool using a pusher member. The fastener is ejected from the fastener delivery tool by depressing an actuator.

In still another embodiment, a fastener delivery tool is provided that includes a loading chamber for receiving at least one fastener having a plurality of tines in a relaxed state, the loading chamber including a retaining member comprising a release pin on which said at least one fastener is loaded. The tool further includes an ejection track communicating with the loading chamber and a lever coupled to a tongue and a pusher member. The tongue is engageable with the plurality of tines of the fastener so as to transform the fastener from the relaxed state to a constrained state. The pusher member is also engageable with a proximal end (e.g., a loop portion) of the fastener so as to translate the fastener to a distal tip of the tool. The fastener is then ejected by depressing a trigger or other actuator.

In still another embodiment, a fastener delivery tool is provided that includes a staging area or section in which a plurality of fasteners are loaded. The fasteners may be loaded individually or within a cartridge. Multiple fasteners may be loaded into the tool, thereby permitting the user to eject or "fire" multiple fasteners successively without having to reload between ejections.

Other aspects and features of the present invention will become apparent from consideration of the following description taken in conjunction with the accompanying drawings.

BRIEF DESCRIPTION OF THE DRAWINGS

As seen in FIG. 4(a), the tines of the fastener are closer together due to advancement of the cartridge retainer and coupled spreader.

FIG. 8(a) is a partial top down plan view of the fastener delivery tool of FIG. 1 with the handle and lever removed for clarity, and showing the loading chamber empty and ready for receiving a cartridge containing a fastener.

FIG. 8(b) is a cross-sectional side view of the fastener delivery tool of FIG. 8(a) taken along the line A-A.

FIG. 9(b) is a cross-sectional side view of the fastener delivery tool of FIG. 9(a) taken along the line B-B.

FIG. 10(a) is a partial top down plan view of the fastener delivery tool of FIG. 1 with the handle and lever removed for clarity, and showing the cartridge retainer advanced distally to secure the fastener via a spreader that draws the two tines of the fastener closer to one another.

FIG. 10(b) is a cross-sectional side view of the fastener delivery tool of FIG. 10(a) taken along the line C-C.

FIG. 11(a) is a partial top down plan view of the fastener delivery tool of FIG. 1 with the handle and lever removed for clarity, and showing the tongue advanced distally to drop into a loop portion of the fastener.

FIG. 11(b) is a cross-sectional side view of the fastener delivery tool of FIG. 11(a) taken along the line D-D.

FIG. 12(a) is a partial top down plan view of the fastener delivery tool of FIG. 1 with the handle and lever removed for clarity, and showing additional distal displacement of the tongue to transform the fastener into the U-configuration.

FIG. 12(b) is a cross-sectional side view of the fastener delivery tool of FIG. 12(a) taken along the line E-E.

FIG. 13(a) is a partial top down plan view of the fastener delivery tool of FIG. 1 with the handle and lever removed for clarity, and showing the fastener advanced distally such that the two tines project slightly beyond the distal-most edge of the ejection track of the fastener delivery tool.

FIG. 13(b) is a cross-sectional side view of the fastener delivery tool of FIG. 13(a) taken along the line F-F.

FIG. 14(a) is a partial top down plan view of the fastener delivery tool of FIG. 1 with the handle and lever removed for clarity, and showing the ejection of the fastener from the ejection track of the fastener delivery tool in a U-shaped configuration.

FIG. 14(b) is a cross-sectional side view of the fastener delivery tool of FIG. 14(a) taken along the line G-G.

DETAILED DESCRIPTION

Figure 1:
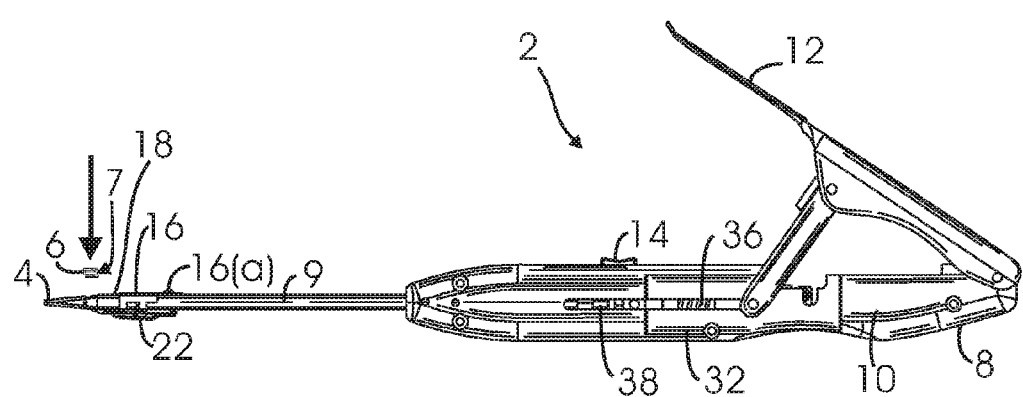
FIG. 1 is a side view of a fastener delivery tool including a cartridge containing a fastener being loaded into a loading chamber of the fastener delivery tool.

Turning to the drawings, FIG. 1 shows a first embodiment of a fastener delivery tool 2. The fastener delivery tool 2 includes a distal tip 4 or snout from which one or more fastener(s) 6 (described in more detail below) may be ejected and a proximal end 8 that may be grasped by a user during positioning and delivery of the fastener 6. The distal tip 4 and proximal end 8 of the tool 2 are separated by an elongated shaft 9. The fastener 6 may be stored within a cartridge 7 that may be loaded into the fastener delivery tool 2. The fastener delivery tool 2 also includes a proximally located handle 10 having a lever 12 or other actuator that may be used to deploy the fastener(s) 6. The handle 10 may be ergonomically shaped such that a user may easily manipulate the fastener delivery tool 2 into position. The handle 10 preferably includes a spring-biased trigger 14, e.g., a depressible button that may be used to eject the fastener 6 from the distal tip 4 of the tool 2.

A cartridge retainer 16 is provided on the shaft 9 that may be movable along the axial direction of the shaft 9. As described more fully below, the cartridge retainer 16 may be used to retain or otherwise secure the cartridge 7 for the subsequent deployment steps of the fastener 6. In addition, the cartridge retainer 16 may transform the fastener 6 into a partially constrained state.

Figure 2A:
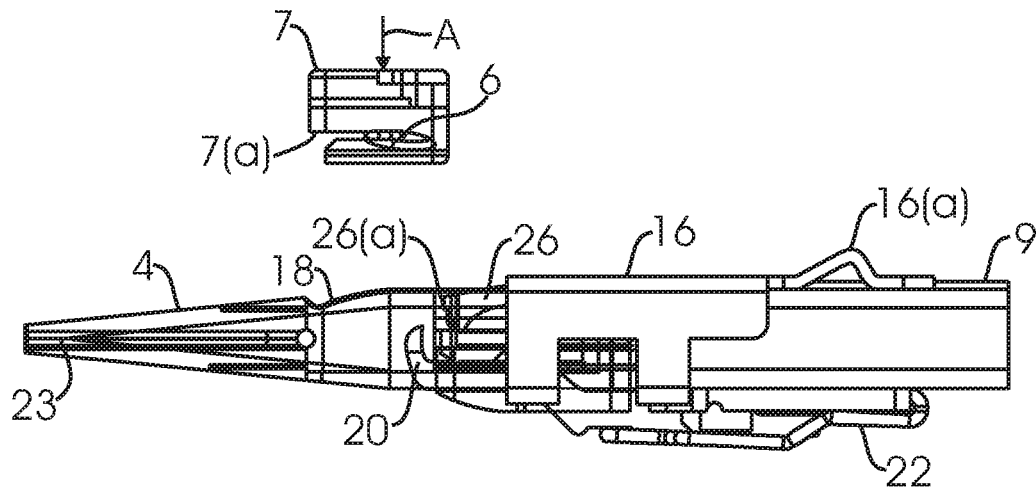
FIG. 2(a) is a cross-sectional side view of the distal tip of the fastener delivery tool shown in FIG. 1, showing the fastener being loaded into the loading chamber (arrow A).
Figure 2B:
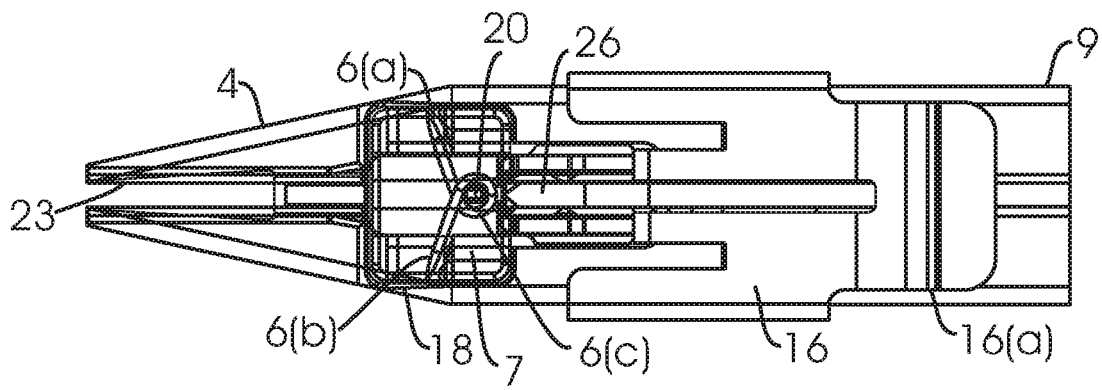
FIG. 2(b) is a cross-sectional top view of the distal tip of the fastener delivery tool shown in FIG. 2(a).

FIGS. 2(*a*) and 2(*b*) illustrate the distal end of the fastener delivery tool 2. As best seen in FIG. 2(*a*), a fastener 6 may be pre-loaded in a cartridge 7, e.g., in a parent or relaxed state. In the relaxed state, the fastener 6 may include a pair of overlapping tines 6(*a*), 6(*b*) (best seen in FIG. 2(*b*)) that may be angled with respect to one another. The fastener 6 further includes a loop portion 6(*c*), e.g., defined by ends of the tines 6(*a*), 6(*b*). In an exemplary embodiment, the fastener 6 may be formed from an elastic or superelastic material, such as a Nickel-Titanium alloy (Nitinol). Additional information on exemplary embodiments of fasteners that may be delivered using the tool 2 are disclosed in co-pending application Ser. No. 10/681,700, filed Oct. 8, 2003, the entire disclosure of which is expressly incorporated by reference herein.

The fastener 6 may be secured or otherwise retained in a groove 7(*a*) or slot in the cartridge 7. The cartridge 7 containing the fastener 6 may be inserted (in the direction of arrow A in FIG. 2(*a*)) into a loading chamber 18 located at the distal end of the shaft 9. During this loading process, the loop portion 6(*c*) of the fastener 6 may be lowered over a retaining member 20. The retaining member 20 may be movable between an engaged state (shown in FIG. 2(*b*)) and a disengaged state (described in more detail below). Preferably, the retaining member 20 is biased in the engaged state by a spring 22 or other biasing mechanism. The retaining member 20 advantageously secures the fastener 6 within the tool 2 during the process of transforming the fastener 6 from the relaxed, parent state to the constrained state (e.g., a U-shaped configuration).

Still referring to FIGS. 2(*a*) and 2(*b*), the distal tip 4 of the tool 2 includes an ejection track 23. The ejection track 23 is connected to or otherwise communicates with the loading chamber 18. During deployment of the fastener 6, the tines 6(*a*), 6(*b*) may be forced into the U-shaped configuration and the fastener 6 may be advanced from the loading chamber 18 and into the ejection track 23 (described in more detail below).

Figure 3A:
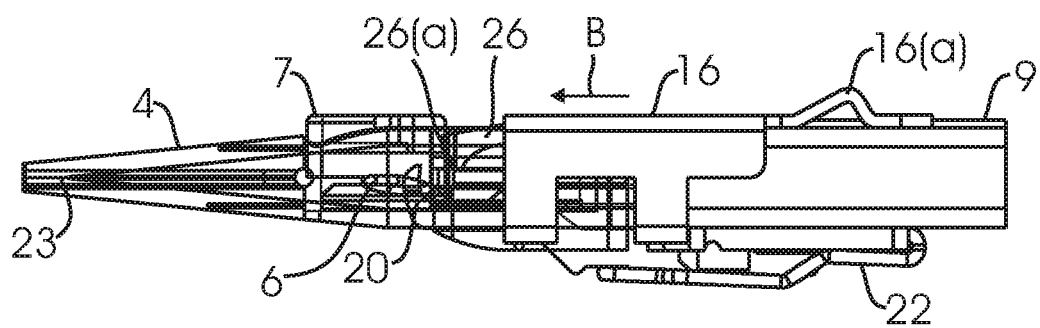
FIG. 3(a) is a cross-sectional side view of the distal tip of the fastener delivery tool shown in FIG. 1, showing initial advancement of the cartridge retainer in the distal direction (arrow B).
Figure 3B:
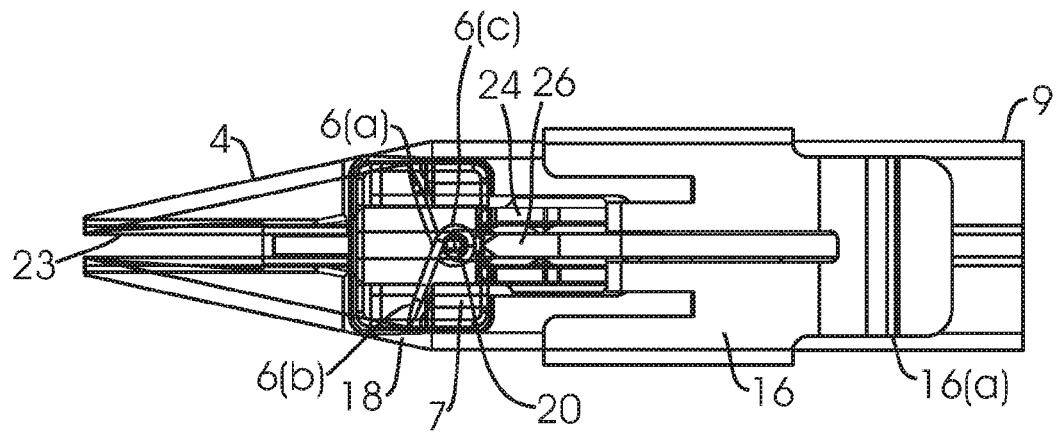
FIG. 3(b) is a cross-sectional top view of the distal tip of the fastener delivery tool shown in FIG. 3(a).
Figure 4A:
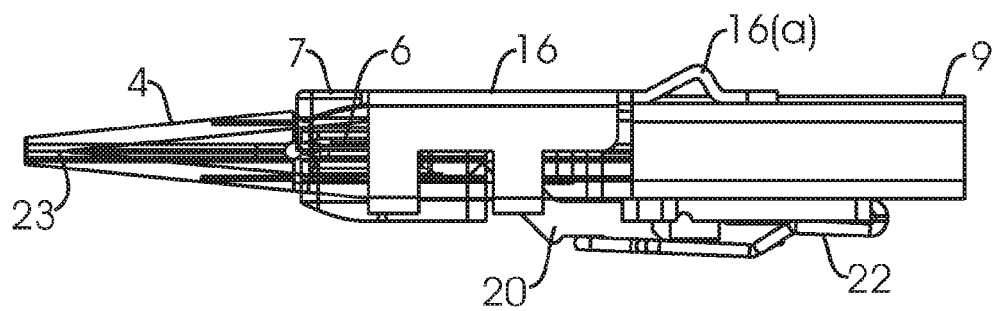
FIG. 4(a) is a cross-sectional side view of the distal tip of the fastener delivery tool shown in FIG. 1, showing complete advancement of the cartridge retainer.
Figure 4B:
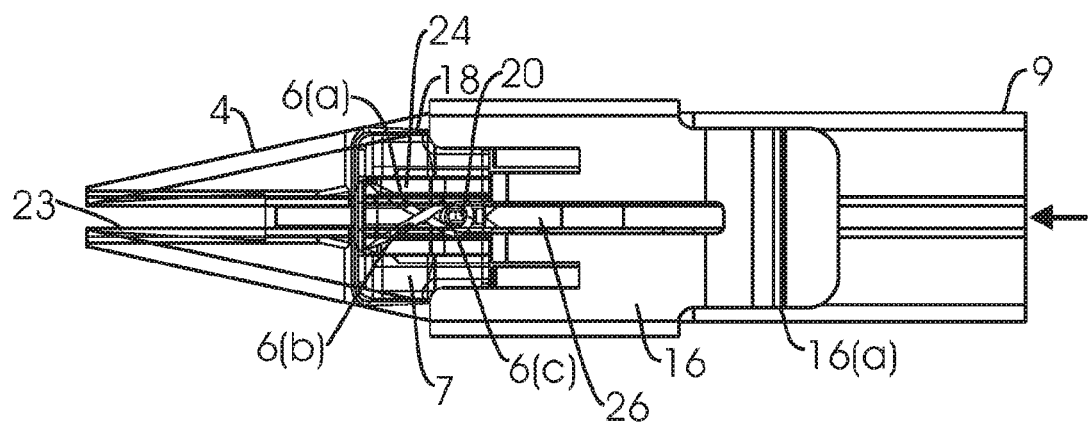
FIG. 4(b) is a cross-sectional top view of the distal tip of the fastener delivery tool shown in FIG. 4(a), showing initial advancement of the tongue in the distal direction.

FIGS. 3(*a*) and 3(*b*) illustrate the next step involved in deploying the fastener 6. As seen in FIGS. 3(*a*) and 3(*b*), the cartridge retainer 16 may be advanced distally (shown by arrow B in FIG. 3(*a*)). In one embodiment, the cartridge retainer 16 may be advanced manually, for example, by depressing a finger on ridge 16(*a*). Alternatively, the cartridge retainer 16 may also be advanced automatically, for example, through movement of the handle 10. The cartridge retainer 16 is coupled to a spreader 24 that may engage the tines 6(*a*), 6(*b*) of the fastener 6. The spreader 24 may include a slot or groove in which the fastener tines 6(*a*), 6(*b*) may be received. Movement of the cartridge retainer 16 from the position shown in FIGS. 3(*a*) and 3(*b*) to the position shown in FIGS. 4(*a*) and 4(*b*) causes the spreader 24 also to move distally. The spreader 24 contacts the tines 6(*a*), 6(*b*) of the fastener 6 and causes the fastener 6 to transform into a partially constrained state (best shown in FIG. 4(*b*)).

Figure 5A:
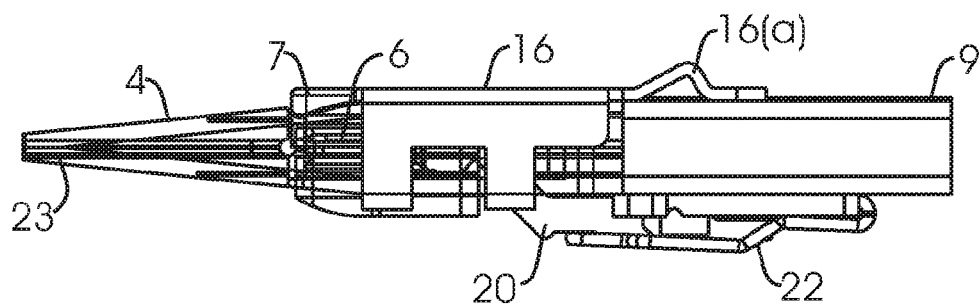
FIG. 5(a) is a cross-sectional side view of the distal tip of the fastener delivery tool shown in FIG. 1, showing a tongue advanced and entering a loop in the fastener.
Figure 5B:
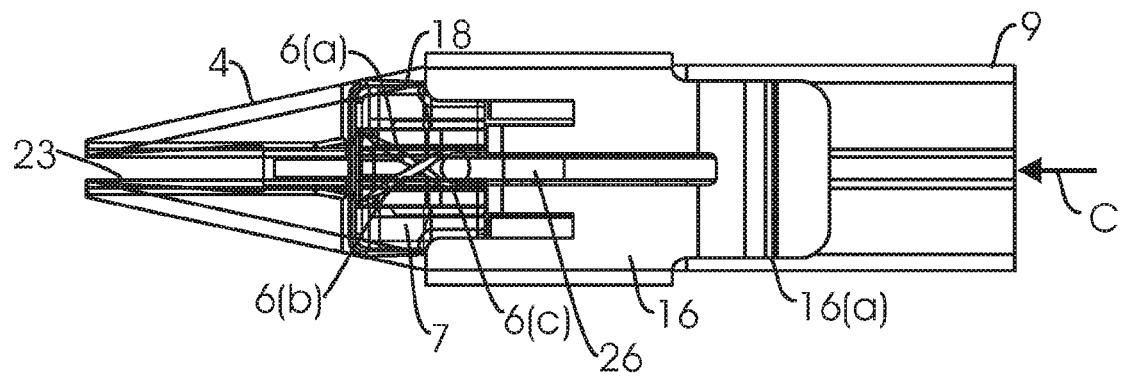
FIG. 5(b) is a cross-sectional top view of the distal tip of the fastener delivery tool shown in FIG. 5(a), showing the tongue entering the loop in the fastener.
Figure 6A:
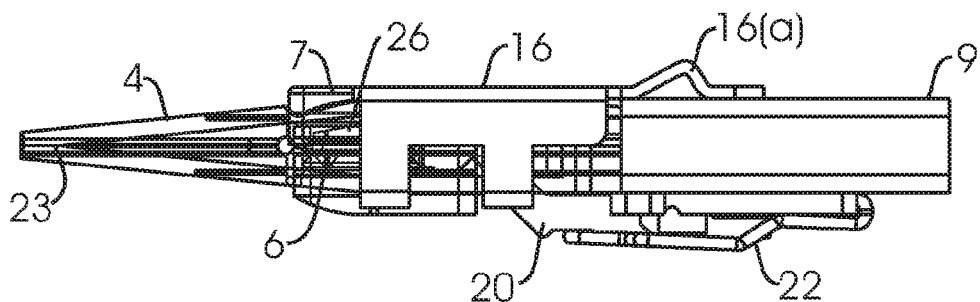
FIG. 6(a) is a cross-sectional side view of the distal tip of the fastener delivery tool shown in FIG. 1, showing transformation of the fastener into a constrained configuration (i.e., the U-configuration). Advancement of the tongue in the distal direction spreads the tines of the fasteners outward to form the U-configuration.
Figure 6B:
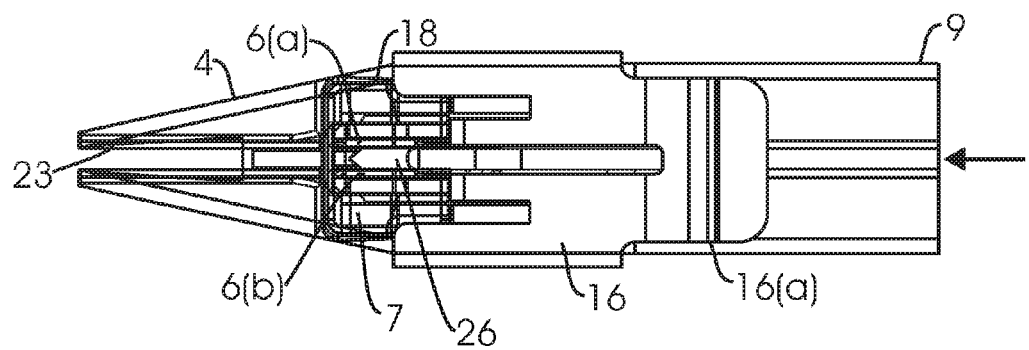
FIG. 6(b) is a cross-sectional top view of the distal tip of the fastener delivery tool shown in FIG. 6(a).

FIGS. 5(*a*) and 5(*b*) illustrate the tongue 26 advancing in the direction of arrow C shown in FIG. 5(*b*). As best seen in FIGS. 2(*a*) and 3(*a*), the tongue 26 includes one or more teeth 26(*a*). The tongue 26 is advanced in the direction of arrow C and the one or more teeth 26(*a*) drop within the loop 6(*c*) of the fastener 6(*c*). FIGS. 5(*a*) and 5(*b*) illustrate the teeth 26(*a*) within the fastener loop 6(*c*). The tongue 26 is advanced further in the distal direction as shown in FIGS. 6(*a*) and 6(*b*) to transform the fastener 6 from the partially constrained state to the fully constrained state (i.e., the U-shaped configuration). The U-shaped configuration is obtained by forcibly parting the tines 6(*a*), 6(*b*) of the fastener 6 using the teeth 26(*a*) of the tongue 26, while restraining the proximal end or loop portion 6(*c*) of the fastener 6.

Figure 7A:
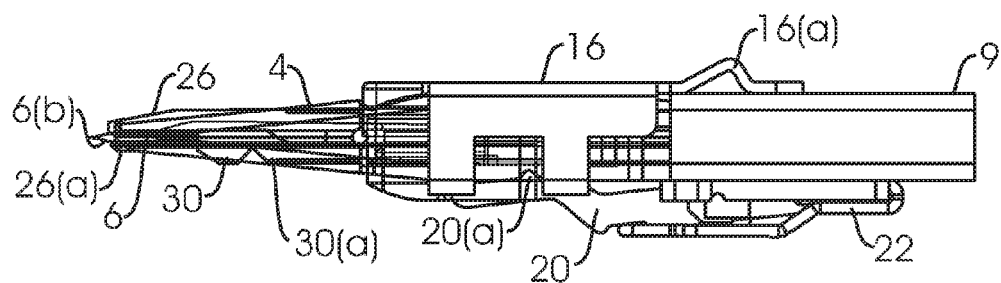
FIG. 7(a) is a cross-sectional side view of the distal tip of the fastener delivery tool shown in FIG. 1, showing translation of the fastener in the distal direction through advancement of a pusher member. The tongue is also translated in the distal direction along with the fastener to aid in maintaining the U-configuration.
Figure 7B:
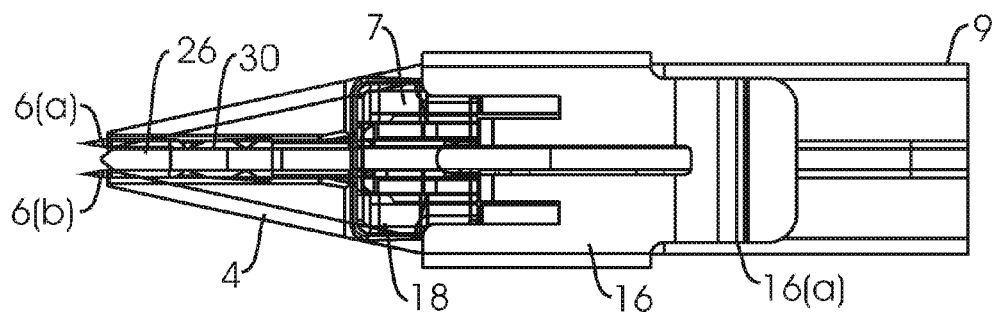
FIG. 7(b) is a cross-sectional top view of the distal tip of the fastener delivery tool shown in FIG. 7(a), showing the tines of the fastener projecting slightly beyond the distal-most end of the fastener delivery tool.

FIGS. 7(*a*) and 7(*b*) illustrate the fastener 6 being advanced through the ejection track 23. After the fastener 6 has assumed the U-shaped configuration, the retaining member 20 may be moved from the engaged state to the disengaged state. FIG. 7(*a*) illustrates the retaining member 20 in the disengaged state. With the retaining member 20 in the disengaged state, the fastener 6 may be free to move distally down the ejection track 23. In one embodiment, the retaining member 20 is moved from the engaged state to the disengaged state by interaction of a cam structure 20(*a*) located on the retaining member 20 with a pusher member 30 (see FIG. 7(*a*)). For example, in the engaged state, the cam structure 20(*a*) on the retaining member 20 may rest within a corresponding groove 30(*a*) in the pusher member 30. When the pusher member 30 is advanced in the distal direction, the cam structure 20(*a*) is forced out of the groove 30(*a*) and forces the retaining member 20 to the disengaged state.

Still referring to FIGS. 7(*a*) and 7(*b*), the pusher member 30 contacts a proximal end of the fastener 6 and pushes or advances the fastener 6 down the ejection track 23. In one embodiment, the pusher member 30 continues to advance the fastener 6 until the fastener 6 reaches a position within the ejection track 23 shown in FIGS. 7(*a*) and 7(*b*). In this position, the fastener 6 is positioned such that the tines 6(*a*), 6(*b*) project slightly from the distal-most end of the tool 2.

This configuration may permit a physician or other user to probe areas of tissue for the optimal insertion location. For example, the physician may probe an area of tissue that may be calcified or plaque-laden and not suitable for placement of a fastener 6. In this regard, the physician may move instead to another more potentially desirable location adjacent the calcified location. Once the desired location is reached, the fastener 6 may be completely ejected from the tool 2, e.g., by depressing the trigger 14 (shown, for example, in FIG. 15(*e*)).

Figure 9A:
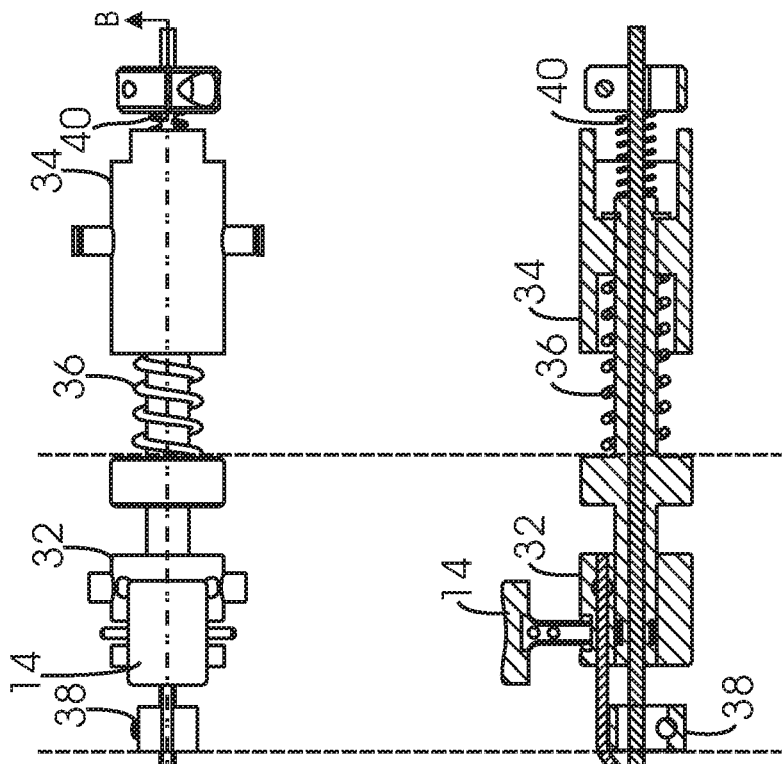
FIG. 9(a) is a partial top down plan view of the fastener delivery tool of FIG. 1 with the handle and lever removed for clarity, and showing a fastener loaded in the loading chamber of the fastener delivery tool.

FIGS. 8(*a*) and 8(*b*) illustrate partial top and side views, respectively, of the fastener delivery tool 2 with the handle 10 and lever 12 removed for clarity. In FIGS. 8(*a*) and 8(*b*), the loading chamber 18 of the device is empty and the cartridge retainer 16 is withdrawn in the proximal direction, permitting loading of another cartridge 7 carrying a fastener 6 into the tool 2. FIGS. 9(*a*) and 9(*b*) illustrate a fastener delivery tool 2 loaded with a single fastener 6 (the cartridge 7 is hidden simply for the sake of clarity). As seen in FIG. 9(*a*), the fastener 6 is in the relaxed or parent state. Referring now to FIGS. 10(*a*) and 10(*b*), the cartridge retainer 16 is then advanced distally to partially constrain the fastener 6 within the spreader 24 (shown in FIG. 10(*a*)).

With reference to FIGS. 11 (*a*) and 11(*b*), additional depression of the lever 12 on the handle 10 advances the tongue 26 such that the teeth 26(*a*) drop into the loop portion 6(*c*) of the fastener (shown best in FIG. 11(*b*)). The tongue 26 is fixedly coupled to a trigger assembly 32 that may be translated distally as the lever 12 on the handle is depressed. The trigger assembly 32 is biased against an advancement mechanism 34 coupled to the actuating lever 12. Actuation of the lever 12 causes the advancement mechanism 34 to displace distally. This distal displacement is translated to the trigger assembly 32 via a spring 36. The spring 36 is preferably stiff such that it acts as a rigid linkage between the advancement mechanism 34 and trigger assembly 32 before the compression stage (discussed in detail below). Translation of the advancement mechanism 34 and trigger assembly 32 (and coupled tongue 26) before the compression stage may be best seen in FIGS. 11(a), 11(b), 12(a), and 12(b).

Referring now to FIGS. 12(a) and 12(b), the fastener 6 is then transformed into the fully constrained state (i.e., U-shaped configuration) by advancing the tongue 26 distally, e.g., by partially depressing the handle 10 of the tool 2. The teeth 26(a) of the tongue 26 may advance between the tines 6(a), 6(b) of the fastener 6 to direct the fastener 6 into the U-shaped configuration. At this stage, the fastener 6 may still be retained by retaining member 20.

FIGS. 13(a) and 13(b) illustrate the trigger assembly 32 abutting and pushing against a clamp 38 that is fixedly coupled to the pusher member 30. Movement of the clamp 38 distally causes corresponding distal movement of the pusher member 30 within the tool 2. The pusher member 30 then advances distally such that the cam 20(a) on the retaining member 20 exits the groove 30(a) in the pusher member, thereby moving the retaining member 20 to the disengaged position. Additional advancement of the handle 12 pushes the fastener 6 down the ejection track 23 of the tool. During this phase of deployment, both the tongue 26 and pusher member 30 move distally in unison. Advancement of the fastener 6 may stop when the tines 6(a), 6(b) project just beyond the distal-most end of the tool 2 (as shown in FIGS. 13(a) and 13(b)).

FIGS. 14(a) and 14(b) illustrate ejection of the fastener 6 from the tool 2. After the spring 36 has been fully compressed and the actuating lever 12 is in the position shown in FIG. 15(e), depression of the trigger 14 (illustrated by arrow D in FIG. 14(b)) causes the pusher member 30 to move rapidly in the distal direction to eject the fastener 6 completely from the ejection track 23. As best seen in FIG. 14(a), the fastener 6 may be ejected in the U-shaped configuration into the adjacent tissue (not shown).

As seen in FIGS. 8 through 14, the tool 2 may also include a proximally located restoring spring 40 to aid in restoring the mechanical linkages (e.g., tongue 26, pusher member 30 and associated trigger assembly 32 and advancement mechanism 34) after the fastener 6 has been ejected from the tool 2.

Figure 15A:
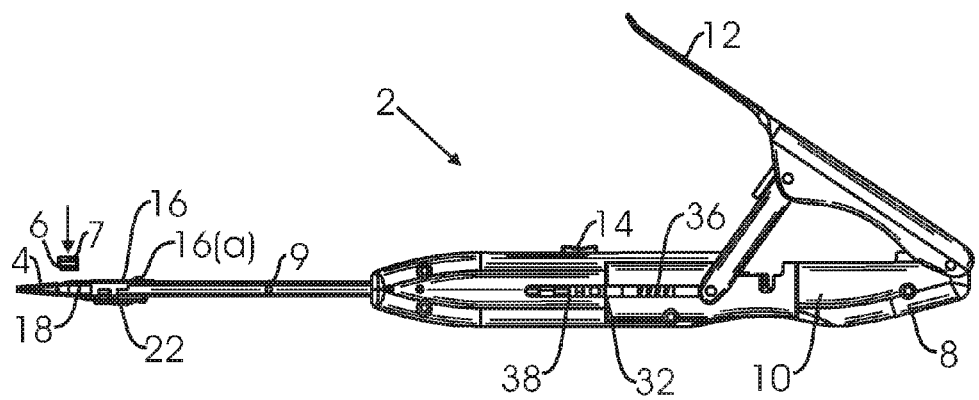
FIG. 15(a) is a side view of a fastener delivery tool according to one aspect of the invention, showing a cartridge being loaded into the loading chamber of the device.
Figure 15B:
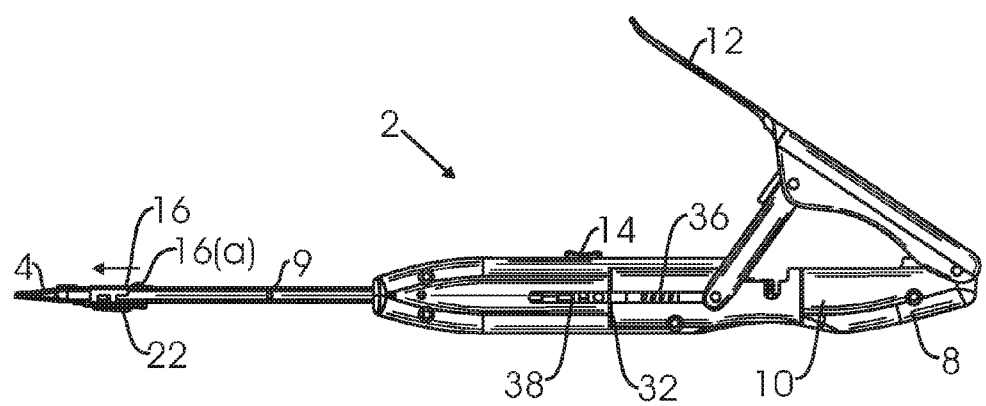
FIG. 15(b) is a side view of a fastener delivery tool shown in FIG. 15(a), showing the cartridge retainer being advanced in the distal direction (see arrow in FIG. 15(b)) over the cartridge.
Figure 15C:
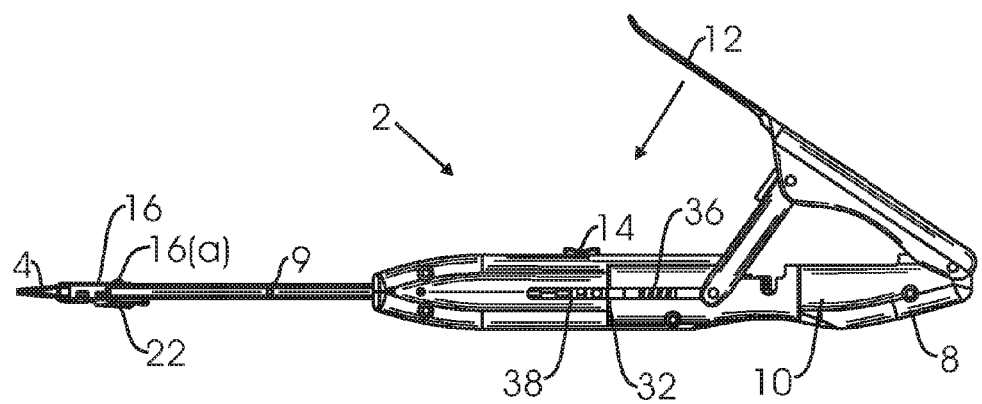
FIG. 15(c) is a side view of a fastener delivery tool shown in FIG. 15(a), showing the fastener being transferred from the cartridge to the distal tip of the fastener delivery tool by actuation of the lever.

FIGS. 15(a) through 15(e) illustrate the various stages of an exemplary method that may be used to deliver a fastener 6 using the fastener delivery tool 2. FIG. 15(a) illustrates a cartridge 7 carrying a fastener 6 being loaded into the loading chamber 18 of the tool 2. FIG. 15(b) illustrates the cartridge retainer 16 being moved distally (in the direction of the arrow in FIG. 15(b)). This movement of the cartridge retainer 16 advances the spreader 24 (not shown in FIG. 15) to place the fastener 6 in a partially constrained state. FIG. 15(c) shows the handle 10 being depressed partially. At this stage, the teeth 26(a) of the tongue 36 drops into the loop portion of the fastener 6 and advances further distally to transform the fastener 6 into the U-shaped configuration. Additional movement of the handle 10 transfers the fastener 6 from the loading chamber 18 to the ejection track 23 in the distal tip 4 of the tool 2.

Figure 15D:
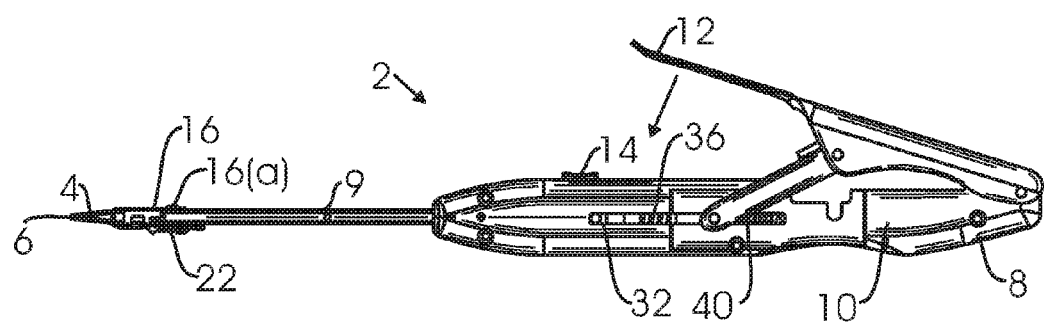
FIG. 15(d) is a side view of a fastener delivery tool shown in FIG. 15(a), showing compression of the ejection spring by additional actuation of the lever.
Figure 15E:
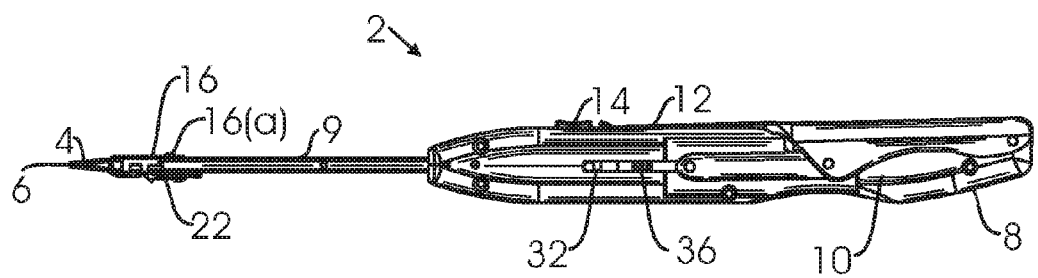
FIG. 15(e) is a side view of a fastener delivery tool shown in FIG. 15(a), showing the fastener delivery tool being fully loaded and ready to deploy the fastener.

FIG. 15(d) illustrates the compression or load-driving step whereby movement of the actuating lever 12 in the direction of the arrow A shown in FIG. 15(d) causes compression of spring 36. FIG. 15(e) illustrates the tool 2 in the fully loaded state. The fastener 6 is disposed at the distal tip 4 of the tool 2 with the tines 6(a), 6(b) projecting distally from the ejection track 23. The spring-loaded trigger 14 is then depressed to eject the fastener 6 completely from the tool 2.

Figure 16A:
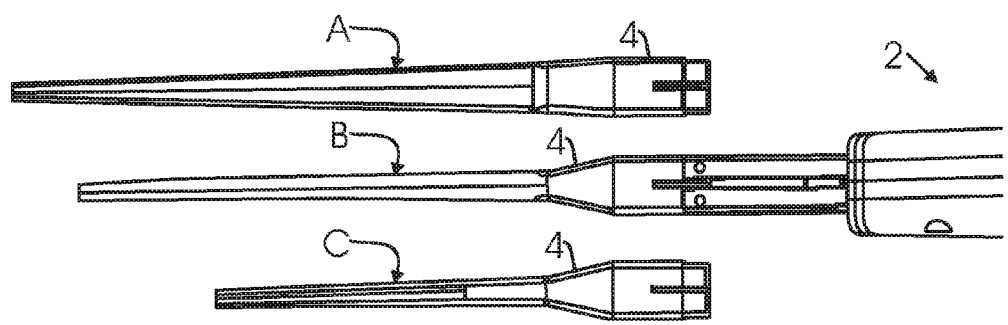
FIGS. 16(a) and 16(b) are top and side views of the distal end of a fastener delivery tool, illustrating exemplary configurations for an elongated distal tip for the tool.
Figure 16B:
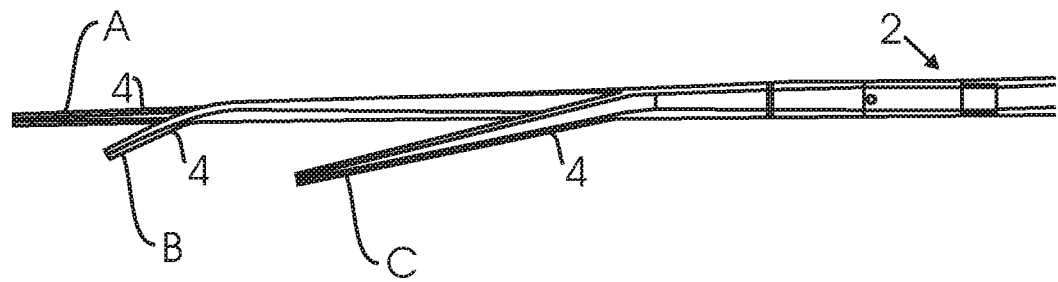

FIGS. 16(a) and 16(b) illustrate alternative configurations, A, B, and C, for an elongated distal tip or snout 4 of the tool 2. The tool 2 may include distal tips 4 of varying lengths in order to facilitate the delivery process. For example, the tips 4 may have lengths between about ten and four hundred millimeters (10-400 mm), or between about five and fifty millimeters (5-50 mm).

The tips 4 may be integrally formed with the tool 2. Alternatively, the tips 4 may be removable and/or interchangeable. In this alternative, the tips 4 and/or tool 2 may include one or more detents or other connectors (not shown) for removably attaching an individual tip 4 to the tool 2. In addition, as best seen in FIG. 16(b), the elongated distal tip or snout 4 may include a variety of geometries or side-profiles, e.g., bends or curves, to increase a user's field of view and/or otherwise facilitate delivering a fastener. Thus, a tip 4 and/or tool 2 may be selected given the particular anatomical presentations encountered during a procedure.

Tip A shown in FIG. 16(b) illustrates a configuration in which the elongated distal tip 4 has a straight or flat profile. Tip B illustrates another configuration in which an intermediate portion of the distal tip 4 is bent or curved out of the plane of the tool 2. The bent or curved configuration is particularly helpful in delivering the fastener 6 generally normal or perpendicular to the surface of the surrounding tissue 90. Tip C illustrates another configuration in which the distal tip 4 is angled with respect to the longitudinal direction of the tool 2.

Figure 17A:
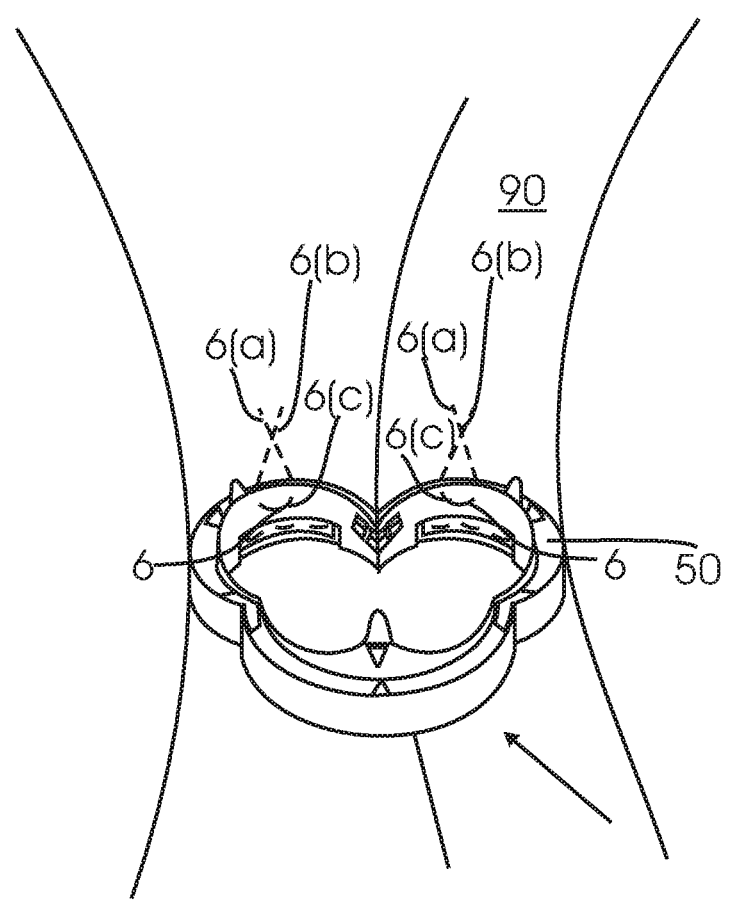
FIG. 17(a) is a cross-section of a patient's body, showing a prosthetic valve secured within a tissue annulus by exemplary fasteners.
Figure 17B:
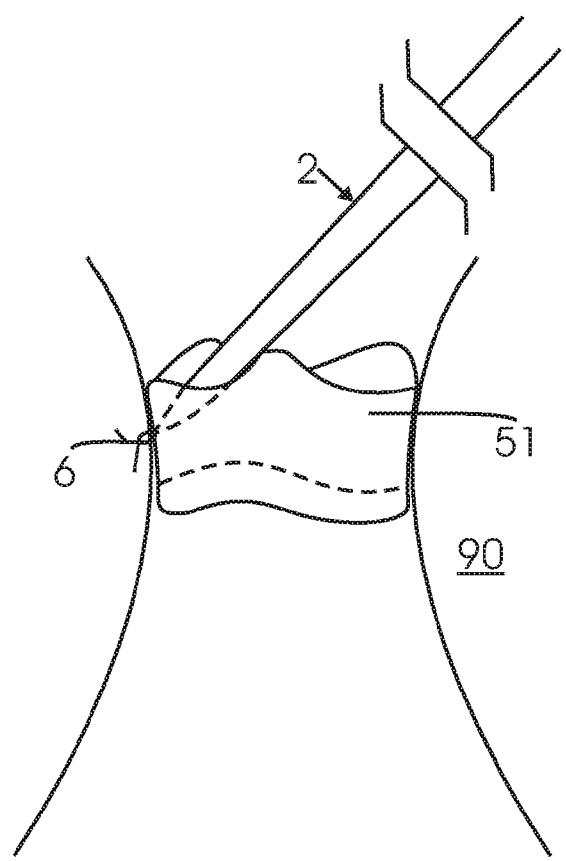
FIG. 17(b) is a cross-section of a patient's body, showing a fastener delivery tool delivering a fastener through a portion of a prosthetic valve into the surrounding tissue.
Figure 17C:
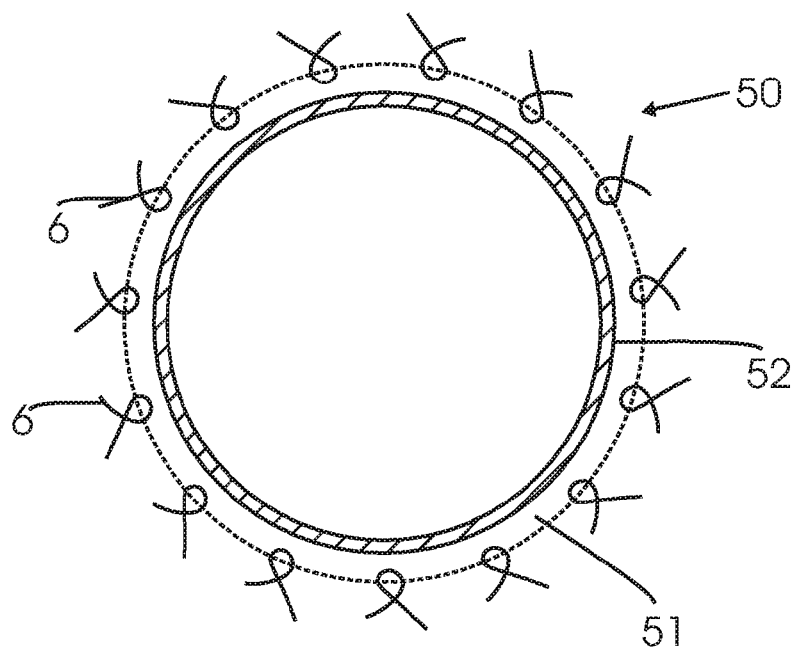
FIG. 17(c) is a radiograph showing a plurality of fasteners deployed about the circumference of a prosthetic valve.

Turning to FIGS. 17(a)-17(c), tool 2 may be used to deliver one or more fasteners 6, e.g., during a heart valve replacement procedure. For example, the tool 2 may be used to deliver a plurality of fasteners 6 through a sewing cuff or ring 51 of a prosthetic heart valve 50 into surrounding tissue. Alternatively, it will be appreciated that the tool 2 may be used to deliver one or more fasteners 6, e.g., to secure other devices to tissue or to another device, or to secure tissue structures together.

As shown, the prosthetic valve 50 is a multiple component prosthesis, e.g., including a gasket member 52 (around which the sewing cuff 51 may extend), and a valve member or "crown" (not shown, e.g., including a frame and a plurality of leaflets, not shown). Exemplary embodiments of single or multiple component prosthetic heart valve assemblies that may be implanted using the tool 2 are disclosed in U.S. Pat. No. 6,371,983 and in co-pending application Ser. Nos. 10/327,821, filed Dec. 20, 2002, and 10/765,725, filed Jan. 26, 2004. The entire disclosures of these references are expressly incorporated by reference herein.

Initially, the gasket member 52 may be advanced into the annulus 90, e.g., by a separate tool (not shown), and maintained at a desired location, e.g., at a site from which native valve leaflets have been removed. The distal tip 4 of the tool 2 (loaded with a fastener 6) may be placed against the sewing cuff 51 with the tip 4 substantially perpendicular to the sewing cuff 51. The tool 2 may be actuated, e.g., by activating the lever 12 and/or trigger 14, to deliver the fastener 6 through the sewing cuff 51 into the underlying tissue. Once the fastener 6 is ejected from the distal tip 4, the tines of the fastener 6 may at least partially recross within the tissue, thereby capturing a portion of the sewing cuff 51 and the underlying tissue within the loop of the fastener. A plurality of fasteners 6 may be successively delivered about a circumference of the sewing cuff 51 to affix the prosthetic valve 50 to the surrounding tissue 90.

FIG. 17(a) illustrates two exemplary fasteners 6 in the fully deployed state. As shown in FIG. 17(a), after penetrating the sewing cuff 51 and underlying tissue, the fasteners 6 may be biased to revert towards the parent or unconstrained state (in which the tines of the fasteners 6 at least partially overlap). In this regard, the prosthetic valve 50 may be fixedly secured to the surrounding tissue 90.

FIG. 17(c) illustrates an exemplary image from a radiography device (not shown), illustrating a plurality of fasteners 6 deployed about the circumference of the prosthetic valve 50. The fasteners 6 and a portion of the gasket member 52 are at least partially radiopaque, and may be seen on a radiograph, while the sewing cuff 51 (shown in phantom in FIG. 17(c)) may be substantially radiolucent, and therefore not visible on the radiograph.

Optionally, the fasteners 6 may be removable from tissue 90 and prosthetic valve 50, e.g., if it is desired to remove the valve 50 or relocate a particular fastener. For example, a pliers-like tool (not shown) may be used to remove a fastener after ejection of the fastener 6 from the tool 2, e.g., if the fastener 6 is oriented incorrectly or the fastener 6 does not penetrate deeply enough into the tissue 90. The physician grasp the loop portion 6(c) of the fastener 6, which may remain at least partially exposed, using the pliers-like tool. The fastener 6 may then be pulled or otherwise retracted proximally to remove the tines of the fastener 6 from the delivery site. A replacement fastener 6 may be loaded into the tool 2 and/or delivered to the delivery site, similar to the methods described above.

Figure 18:
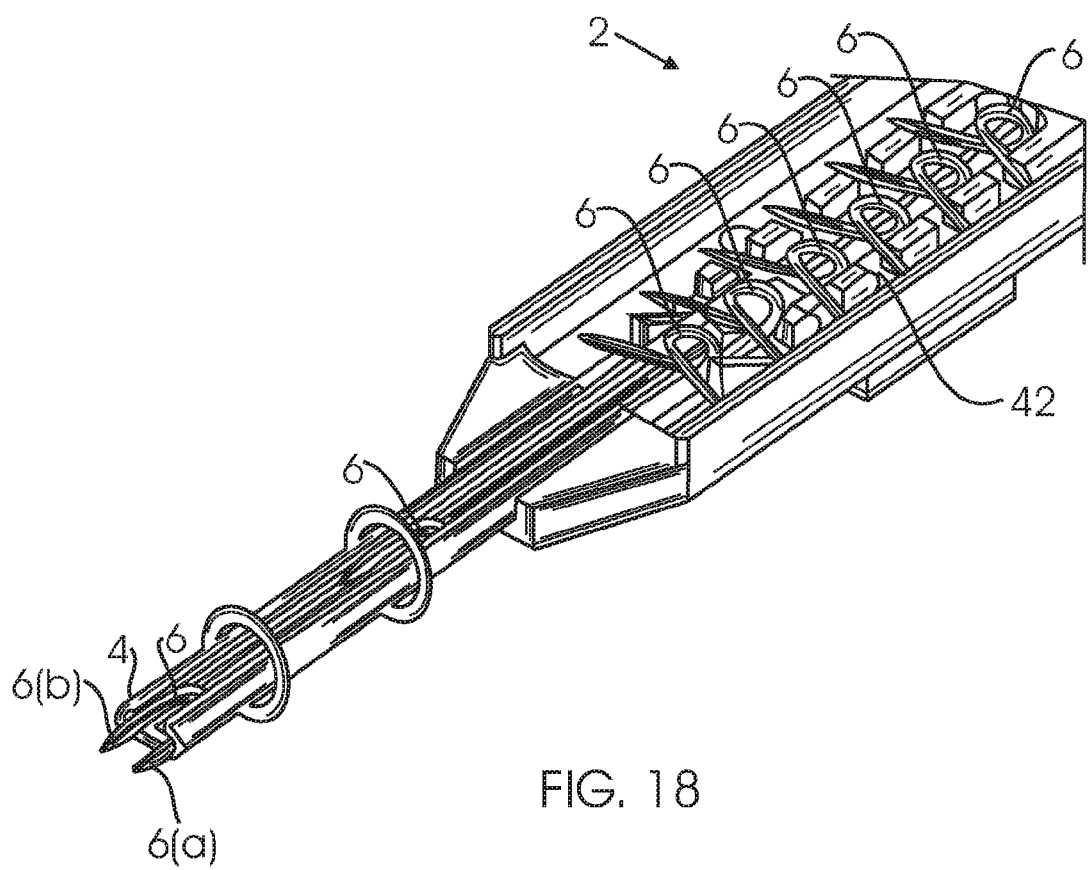
FIG. 18 is an alternative embodiment of a fastener delivery tool that houses a plurality of fasteners.

In an alternative embodiment, a tool may be provided that may accommodate loading multiple fasteners 6 into the tool 2 simultaneously or successively before delivery. Such a tool 2 may be desirable because the tool 2 does not have to be removed from the body cavity to load successive fasteners 6, which may accelerate delivery of the fasteners 6. FIG. 18 illustrates an embodiment of a tool 2, showing a plurality of fasteners 6 loaded into a staging area or section 42. The fasteners 6 may be advanced successively in the distal direction toward the distal tip 4 of the tool 2. A cartridge (not shown) may be provided that holds a plurality of fasteners 6 such that the tool 2 may be loaded with multiple fasteners 6 simply by loading a single cartridge into the tool 2.

While embodiments of the present invention have been shown and described, various modifications may be made without departing from the scope of the present invention. The invention, therefore, should not be limited, except to the following claims, and their equivalents.

We claim:

1. A fastener delivery tool, comprising:
    a loading chamber for receiving a fastener including a plurality of tines overlapping one another to define a loop in a relaxed state;
    a releasable retaining member receivable in the loop for limiting movement of the fastener within the loading chamber;
    an ejection track communicating with the loading chamber;
    a handle including an actuator; and
    a tongue and a pusher member coupled to the actuator, wherein activation of the actuator advances the tongue for engaging the tines for transforming the fastener from the relaxed state to a constrained state and advances the pusher member for advancing the fastener from the loading chamber down the ejection track, and
    wherein the tongue comprises one or more teeth configured to drop within the loop when the actuator is activated, the tongue configured to advance distally along inner surfaces of the tines for parting the tines with the one or more teeth.

2. The fastener delivery tool of claim 1, further comprising a trigger for ejecting the fastener distally from the ejection track.

3. The fastener delivery tool of claim 1, wherein, in the constrained state, the fastener comprises a U-shape.

4. The fastener delivery tool of claim 3, wherein the ejection track comprises side walls for constraining the fastener in the U-shape as the fastener is advanced down the ejection track.

5. The fastener delivery tool of claim 4, wherein the tines are exposed distally beyond the ejection track when the actuator is activated without ejecting the fastener completely from the ejection track.

6. The fastener delivery tool of claim 1, wherein the retaining member comprises a movable release pin.

7. The fastener delivery tool of claim 6, wherein the release pin is coupled to at least one of the tongue and the pusher member such that the release pin releases the fastener after the actuator is activated.

8. The fastener delivery tool of claim 1, further comprising a staging section configured to receive a plurality of fasteners disposed therein.

9. The fastener delivery tool of claim 8, further comprising a cartridge receivable in the staging section configured to carry the plurality of fasteners.

10. The fastener delivery tool of claim 1, the retaining member being releasable upon engagement with a cam located on the pusher member.

11. The fastener delivery tool of claim 1, wherein the fastener includes two tines that overlap one another in the relaxed state.

12. The fastener delivery tool of claim 1, wherein the fastener is biased towards the relaxed state such that the tines at least partially overlap when the fastener is ejected from the ejection track.

13. The fastener delivery tool of claim 3, wherein the tongue comprises one or more teeth that drop within the loop wherein when the actuator is activated, the tongue being advanced distally such that the one or more teeth part the tines to define the U-shaped configuration.

14. A fastener delivery tool, comprising:
    a loading chamber for receiving at least one fastener having a pair of tines overlapping one another to define a loop in a relaxed state, the loading chamber including a release pin for loading said at least one fastener so that the pin is receivable in the loop;
    an ejection track communicating with the loading chamber; and
    an actuator coupled to a tongue and a pusher member,
    wherein activation of the actuator advances the tongue for engaging the pair of tines for transforming the fastener from the relaxed state to a constrained state and advances the pusher member for advancing the at least one fastener in the constrained state from the loading chamber down the ejection track, and
    wherein the tongue comprises one or more teeth configured to drop within the loop when the actuator is activated, the tongue configured to advance distally along inner surfaces of the tines for parting the tines with the one or more teeth.

15. The fastener delivery tool of claim 14, wherein the at least one fastener has a U-shape in the constrained state.

16. The fastener delivery tool of claim 15, wherein the ejection track comprises side walls for constraining the at least one fastener in the U-shape as the at least one fastener is advanced down the ejection track.

17. The fastener delivery tool of claim 15, wherein when the actuator is activated, the tongue being advanced distally such that the one or more teeth part the tines to define the U-shaped configuration.

18. The fastener delivery tool of claim 14, further comprising a trigger for ejecting the at least one fastener from the ejection track.

* * * * *

UNITED STATES PATENT AND TRADEMARK OFFICE
CERTIFICATE OF CORRECTION

| | |
|---|---|
| PATENT NO. | : 8,500,755 B2 |
| APPLICATION NO. | : 12/022898 |
| DATED | : August 6, 2013 |
| INVENTOR(S) | : Ino et al. |

Page 1 of 1

It is certified that error appears in the above-identified patent and that said Letters Patent is hereby corrected as shown below:

In the Claims

In column 10, line 54, claim no. 14 "tines for transforming the fastener" should read -- tines for transforming the at least one fastener --

Signed and Sealed this
Thirtieth Day of December, 2014

Michelle K. Lee
*Deputy Director of the United States Patent and Trademark Office*